(12) United States Patent
Dotan et al.

(10) Patent No.: US 7,842,086 B2
(45) Date of Patent: Nov. 30, 2010

(54) MIRROR IMPLANT

(75) Inventors: Gideon Dotan, Yehud (IL); Yossi Gross, Moshav Mazor (IL); Eli Aharoni, Tel Aviv (IL)

(73) Assignee: Visioncare Ophthalmic Technologies, Inc., Saratoga, CA (US)

( * ) Notice: Subject to any disclaimer, the term of this patent is extended or adjusted under 35 U.S.C. 154(b) by 991 days.

(21) Appl. No.: 11/031,969

(22) Filed: Jan. 7, 2005

(65) Prior Publication Data

US 2006/0155374 A1    Jul. 13, 2006

(51) Int. Cl.
*A61F 2/16* (2006.01)
(52) U.S. Cl. ............... 623/6.17; 623/6.26; 623/6.32
(58) Field of Classification Search ............ 623/6.32, 623/6.17, 6.11, 6.56, 6.26
See application file for complete search history.

(56) References Cited

U.S. PATENT DOCUMENTS

| | | | |
|---|---|---|---|
| 3,515,461 A * | 6/1970 | Rayces et al. ............. 359/731 |
| 4,056,855 A | 11/1977 | Kelman |
| 4,292,272 A * | 9/1981 | Kitajima et al. ............. 422/57 |
| 4,337,222 A * | 6/1982 | Kitajima et al. ............. 422/56 |
| 4,463,458 A | 8/1984 | Seidner |
| 4,527,294 A | 7/1985 | Heslin |
| 4,581,031 A * | 4/1986 | Koziol et al. ............. 623/6.26 |
| 4,596,578 A | 6/1986 | Kelman |
| 4,612,290 A * | 9/1986 | Yazawa et al. ............. 436/97 |
| 4,666,446 A | 5/1987 | Koziol et al. |
| 4,710,197 A | 12/1987 | Donn et al. |
| 4,731,078 A | 3/1988 | Stoy et al. |
| 4,743,254 A | 5/1988 | Davenport |
| 4,759,761 A * | 7/1988 | Portnoy ............. 623/6.11 |
| 4,833,890 A | 5/1989 | Kelman |
| 4,892,543 A | 1/1990 | Turley |
| 4,911,714 A | 3/1990 | Poley |
| 4,911,715 A | 3/1990 | Kelman |
| 5,026,396 A | 6/1991 | Darin |
| 5,044,743 A | 9/1991 | Ting |
| 5,108,429 A | 4/1992 | Wiley |
| 5,222,981 A | 6/1993 | Werblin |
| 5,391,202 A | 2/1995 | Lipshitz et al. |

(Continued)

FOREIGN PATENT DOCUMENTS

EP    0162573    11/1985

(Continued)

OTHER PUBLICATIONS

Abstract of French patent FR-2666735 published Mar. 20, 1992.*

(Continued)

*Primary Examiner*—Paul Prebilic
(74) *Attorney, Agent, or Firm*—Fish & Richardson P.C.

(57) ABSTRACT

An intraocular implant including a plurality of mirrors, including mirrors having optical power, being operative, when the implant is implanted, for receiving light from a scene and focusing the light onto a retina, the mirrors containing bio-incompatible materials and at least one hermetically sealed enclosure, enclosing the plurality of mirrors, and being operative, when the implant is implanted, to seal the bio-incompatible materials from the interior of the eye, without interfering with the passage of light therethrough from the scene to the plurality of mirrors and from the plurality of mirrors to the retina.

7 Claims, 9 Drawing Sheets

U.S. PATENT DOCUMENTS

| | | | |
|---|---|---|---|
| 5,405,387 | A | 4/1995 | Sodero |
| 5,628,798 | A | 5/1997 | Eggleston et al. |
| 5,653,751 | A | 8/1997 | Samiy et al. |
| 5,774,202 | A * | 6/1998 | Abraham et al. ............ 351/177 |
| 5,814,103 | A | 9/1998 | Lipshitz et al. |
| 5,876,442 | A | 3/1999 | Gross et al. |
| 5,928,283 | A | 7/1999 | Gross et al. |
| 5,964,802 | A | 10/1999 | Anello et al. |
| 6,132,958 | A * | 10/2000 | Simon ........................ 435/4 |
| 6,197,057 | B1 * | 3/2001 | Peyman et al. ............ 623/6.32 |
| 6,358,280 | B1 | 3/2002 | Herrick |
| 6,400,989 | B1 | 6/2002 | Eckmiller |
| 6,569,199 | B1 | 5/2003 | Dotan et al. |
| 6,847,847 | B2 | 1/2005 | Nisch et al. |
| 6,849,090 | B2 | 2/2005 | Nigam |
| 6,902,577 | B2 * | 6/2005 | Lipshitz et al. ............ 623/6.31 |
| 6,913,620 | B2 * | 7/2005 | Lipshitz ..................... 623/6.32 |
| 7,008,448 | B2 * | 3/2006 | Lipshitz et al. ............ 623/6.31 |
| 7,079,900 | B2 | 7/2006 | Greenburg et al. |
| 7,276,080 | B2 * | 10/2007 | Murakami et al. .......... 623/6.3 |
| 2002/0143395 | A1 | 10/2002 | Skottun |
| 2002/0173846 | A1 | 11/2002 | Blake et al. |
| 2003/0060881 | A1 | 3/2003 | Glick et al. |
| 2003/0078656 | A1 | 4/2003 | Nguyen |
| 2003/0105522 | A1 | 6/2003 | Glazier |
| 2003/0187502 | A1 * | 10/2003 | Lipshitz ..................... 623/6.11 |
| 2003/0187503 | A1 * | 10/2003 | Lipshitz et al. ............ 623/6.22 |
| 2004/0117011 | A1 * | 6/2004 | Aharoni et al. ............ 623/6.11 |
| 2004/0148022 | A1 | 7/2004 | Eggleston |
| 2004/0181279 | A1 | 9/2004 | Nun |
| 2004/0236421 | A1 * | 11/2004 | Lipshitz et al. ............ 623/6.27 |
| 2005/0071002 | A1 | 3/2005 | Glazier |
| 2006/0155374 | A1 * | 7/2006 | Dotan et al. ............... 623/6.26 |

FOREIGN PATENT DOCUMENTS

| | | |
|---|---|---|
| EP | 0242043 | 10/1987 |
| EP | 0897 702 A2 | 2/1999 |
| EP | 1438930 | 7/2004 |
| EP | 1475055 | 11/2004 |
| FR | 2713082 | 6/1995 |
| GB | 877083 | 9/1961 |
| WO | WO 83/01566 | 5/1983 |
| WO | WO-0004849 | 2/2000 |
| WO | WO 00/38593 | 7/2000 |

OTHER PUBLICATIONS

European Search Report Application No. EP 04 25 0124, dated May 28, 2004 (3 pages).

An Office Action dated Jan. 13, 2009, which issued during the prosecution of Applicant's U.S. Appl. No. 11/420,327.

An Office Action dated Jan. 20, 2009, which issued during the prosecution of Applicant's Japanese Patent Application No. 2004-7118.

An International Search Report dated Feb. 26, 2007, which issued during the prosecution of Applicant's PCT Patent Application No. PCT/IL06/00873.

An Office Action dated Aug. 29, 2009, which issued during the prosecution of Applicant's Canadian Patent Application No. 2,455,076.

An Office Action dated Sep. 8, 2009, which issued during the prosecution of Applicant's Japanese Patent Application No. 2004-560169.

An Office Action dated Sep. 9, 2009, which issued during the prosecution of Applicant's U.S. Appl. No. 11/069,581.

* cited by examiner

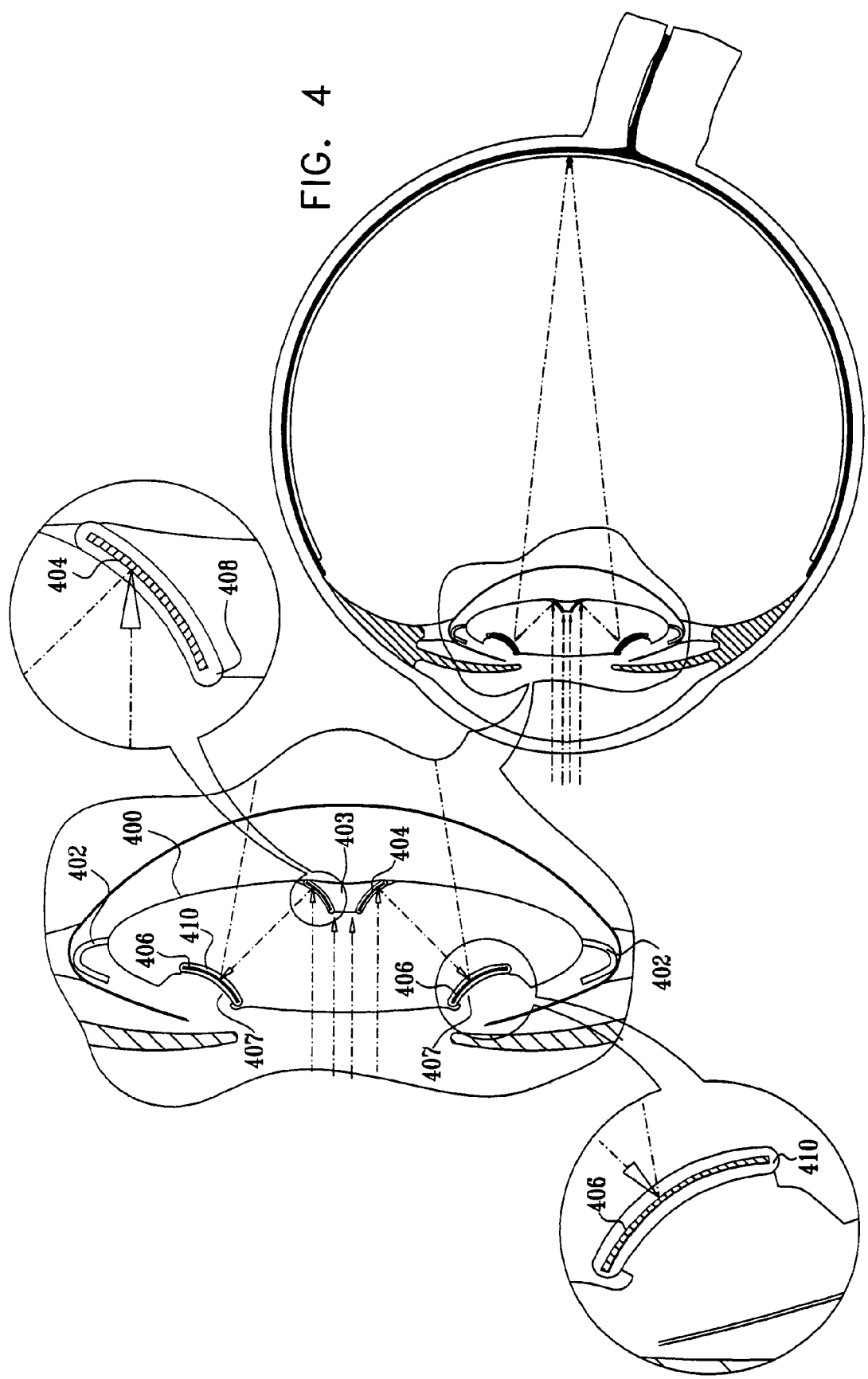

MIRROR IMPLANT

REFERENCE TO CO-PENDING APPLICATIONS

Applicants hereby make reference to the following co-pending U.S. Patent Applications, the disclosures of which are hereby incorporated by reference:

U.S. Ser. No. 10/321,793, filed Dec. 17, 2002, entitled "Intraocular Implants"; U.S. Ser. No. 10/342,160, filed Jan. 14, 2003, entitled "Intraocular Lens Implant" and U.S. Ser. No. 10/489,388, filed Mar. 11, 2004, entitled "Intraocular Implants."

FIELD OF THE INVENTION

The present invention relates to ocular implants generally and more particularly to intraocular implants.

BACKGROUND OF THE INVENTION

The following patent publications are believed to represent the current state of the art:

U.S. Pat. Nos. 5,354,335; 5,814,103; 5,876,442; 5,928,283; 6,007,579; 6,066,171; 5,653,751; 6,596,026; 6,569,199; 6,464,725; 5,391,202; 5,384,606; 4,074,368; 4,994,082; 5,628,798; 5,222,981; 4,172,297; 5,769,890; 4,892,543; 4,373,218; 4,968,127; 4,759,761; 4,976,732 and 5,769,889;

Published U.S. Application 2001/018,612;

Published PCT Applications WO 94/07,435; WO 00/38593 and WO 83/01566;

Foreign Patent Publications DE 4,403,326; EP 1,092,402; EP 0,419,740; GB 2,181,355; EP 0,897,702; EP 0,212,616; DE 3,428,895 and DE 19,501,444.

SUMMARY OF THE INVENTION

The present invention seeks to provide an improved intraocular implant.

There is thus provided in accordance with a preferred embodiment of the present invention an intraocular implant including a plurality of mirrors, including mirrors having optical power, being operative, when the implant is implanted, for receiving light from a scene and focusing the light onto a retina, the mirrors containing bio-incompatible materials and at least one hermetically sealed enclosure, enclosing the plurality of mirrors, and being operative, when the implant is implanted, to seal the bio-incompatible materials from the interior of the eye, without interfering with the passage of light therethrough from the scene to the plurality of mirrors and from the plurality of mirrors to the retina.

Preferably, the implant is formed as a transparent body, the plurality of mirrors is formed by coating surfaces of the transparent body and the at least one hermetically sealed enclosure is formed by a layer of transparent material, which is non-permeable to the bio-incompatible material, formed over the plurality of mirrors and the transparent body. Additionally, the layer of transparent material is selected to be one of glass and transparent sprayable material.

Preferably, the intraocular implant also includes at least one iris restrictor operative to restrict closing of the iris, thereby to ensure that the light from a scene reaches the plurality of mirrors. Additionally, the at least one iris restrictor includes a prism. In accordance with another preferred embodiment the prism is operative to direct the light onto one of the plurality of mirrors. Alternatively, the prism is operative to change the direction of the light and to direct it onto at least one of the plurality of mirrors.

Alternatively or additionally, the intraocular implant also includes at least one light restrictor arranged so as to restrict light passing through the implant such that generally only light which impinges on the plurality of mirrors reaches the retina when the implant is implanted.

There is also provided in accordance with another preferred embodiment of the present invention an intraocular implant including a plurality of mirrors, including mirrors having optical power, being operative, when the implant is implanted, for receiving light from a scene and focusing the light onto a retina and at least one iris restrictor operative to restrict closing of the iris, thereby to ensure that the light from a scene reaches the plurality of mirrors.

Preferably, the at least one iris restrictor is joined to the plurality of mirrors. Additionally or alternatively, the at least one iris restrictor includes a prism for changing the direction of light impinging thereonto from a scene and directing it onto at least one of the plurality of mirrors.

Preferably, the at least one iris restrictor is mountable onto an iris. In accordance with another preferred embodiment the at least one iris restrictor includes at least one hook, joined to the plurality of mirrors and engaging the iris at at least one location along an inner peripheral edge thereof.

Preferably, the plurality of mirrors is formed of a bio-incompatible material. Additionally, the plurality of mirrors is hermetically sealed to prevent contamination of the interior of the eye by the bio-incompatible material. Alternatively, each of the plurality of mirrors is hermetically sealed to prevent contamination of the interior of the eye by the bio-incompatible material.

In accordance with another preferred embodiment the intraocular implant also includes at least one light restrictor arranged so as to restrict light passing through the implant such that generally only light which impinges on the plurality of mirrors reaches the retina when the implant is implanted.

There is even further provided in accordance with still another preferred embodiment of the present invention an intraocular implant including a plurality of mirrors, including mirrors having optical power, being operative, when the implant is implanted, for receiving light from a scene and focusing the light onto a retina and at least one light restrictor arranged so as to restrict light passing through the implant such that generally only light which impinges on the plurality of mirrors reaches the retina when the implant is implanted.

There is further provided in accordance with yet another preferred embodiment of the present invention an intraocular implant including a plurality of mirrors, including mirrors having optical power, being operative, when the implant is implanted, for receiving light from a scene and focusing the light onto a retina, the plurality of mirrors being configured so as to be adapted for operation when implanted in an eye of a patient which has undergone refractive surgery.

Preferably, the plurality of mirrors is formed of a bio-incompatible material. Additionally, the plurality of mirrors is hermetically sealed to prevent contamination of the interior of the eye by the bio-incompatible material. Alternatively, each of the plurality of mirrors is hermetically sealed to prevent contamination of the interior of the eye by the bio-incompatible material.

There is yet further provided in accordance with another preferred embodiment of the present invention an intraocular implant including a plurality of mirrors, including mirrors having optical power, being operative, when the implant is implanted, for receiving light from a scene and focusing the light onto a retina, the mirrors containing bio-incompatible materials, at least one hermetically sealed enclosure, enclosing the plurality of mirrors, and being operative, when the implant is implanted, to seal the bio-incompatible materials from the interior of the eye, without interfering with the passage of light therethrough from the scene to the plurality of mirrors and from the plurality of mirrors to the retina, at least one iris restrictor operative to restrict closing of the iris, thereby to ensure that the light from a scene reaches the plurality of mirrors, the at least one iris restrictor including a prism which directs the light to one of the plurality of mirrors and at least one light restrictor arranged so as to restrict light passing through the implant such that generally only light which impinges on the plurality of mirrors reaches the retina when the implant is implanted.

BRIEF DESCRIPTION OF THE DRAWINGS

The present invention will be understood and appreciated more fully from the following detailed description, taken in conjunction with the drawings in which:

FIG. 4 is a simplified sectional illustration of an implanted intraocular implant constructed and operative in accordance with still another preferred embodiment of the present invention;

DETAILED DESCRIPTION OF PREFERRED EMBODIMENTS

Figure 1:
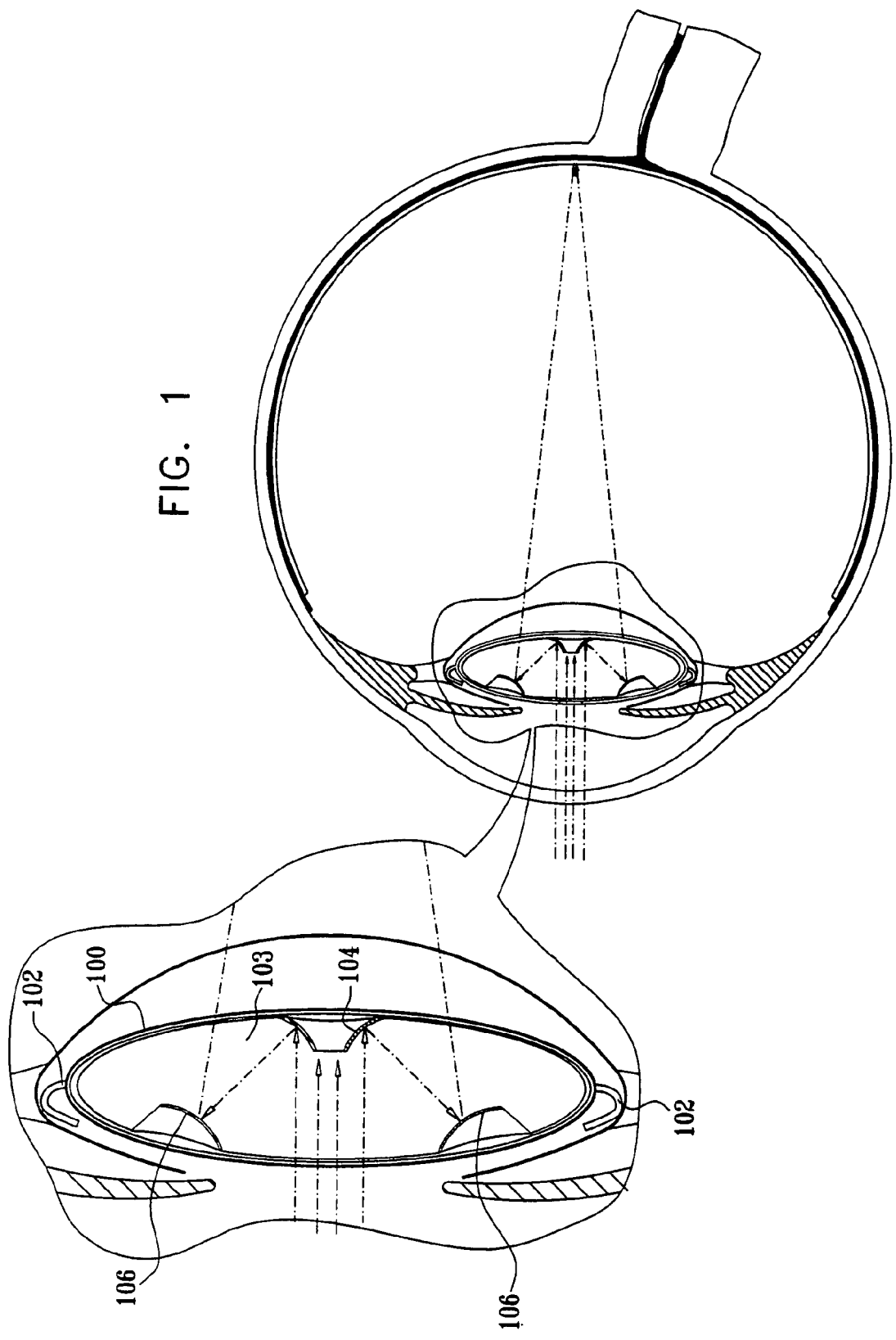
FIG. 1 is a simplified sectional illustration of an implanted intraocular implant constructed and operative in accordance with a preferred embodiment of the present invention.

Reference is now made to FIG. 1, which is a simplified sectional illustration of an implanted intraocular implant constructed and operative in accordance with a preferred embodiment of the present invention. As seen in FIG. 1, the implant preferably comprises a generally light transparent implant enclosure 100, preferably formed of plastic, glass or other suitable bio-compatible transparent material and having a generally oval cross section, as seen in FIG. 1, which is supported by haptics 102. The interior of implant enclosure 100 is hermetically sealed from the outside thereof.

Located within implant enclosure 100 and mounted therein is a transparent implant body 103, preferably formed of rigid plastic, such as PMMA, on which is formed an outwardly facing generally truncated, circumferentially symmetric concave mirror 104. Mirror 104 is operative to reflect and focus light impinging thereon from the outside to an inwardly facing peripherally disposed, circumferentially symmetric convex mirror 106, also formed on body 103, which mirror 106, in turn, directs the light to the retina. It is appreciated that either or both of enclosure 100 and implant body 103 may have optical power and may help direct the light from a scene to the retina.

It is a particular feature of the present invention that mirrors 104 and 106 are employed therein, inasmuch as mirrors 104 and 106 conventionally contain bio-incompatible materials. The hermetic sealing of implant enclosure 100 enables their use in accordance with a preferred embodiment of the present invention and prevents contamination of the interior of the eye by the bio-incompatible materials.

It is appreciated that implant body 103 may include a solid transparent interior or a frame including a hollow interior and may be formed as a sealed transparent capsule or other construction suitable for maintaining mirrors 104 and 106 in proper alignment.

Figure 2:
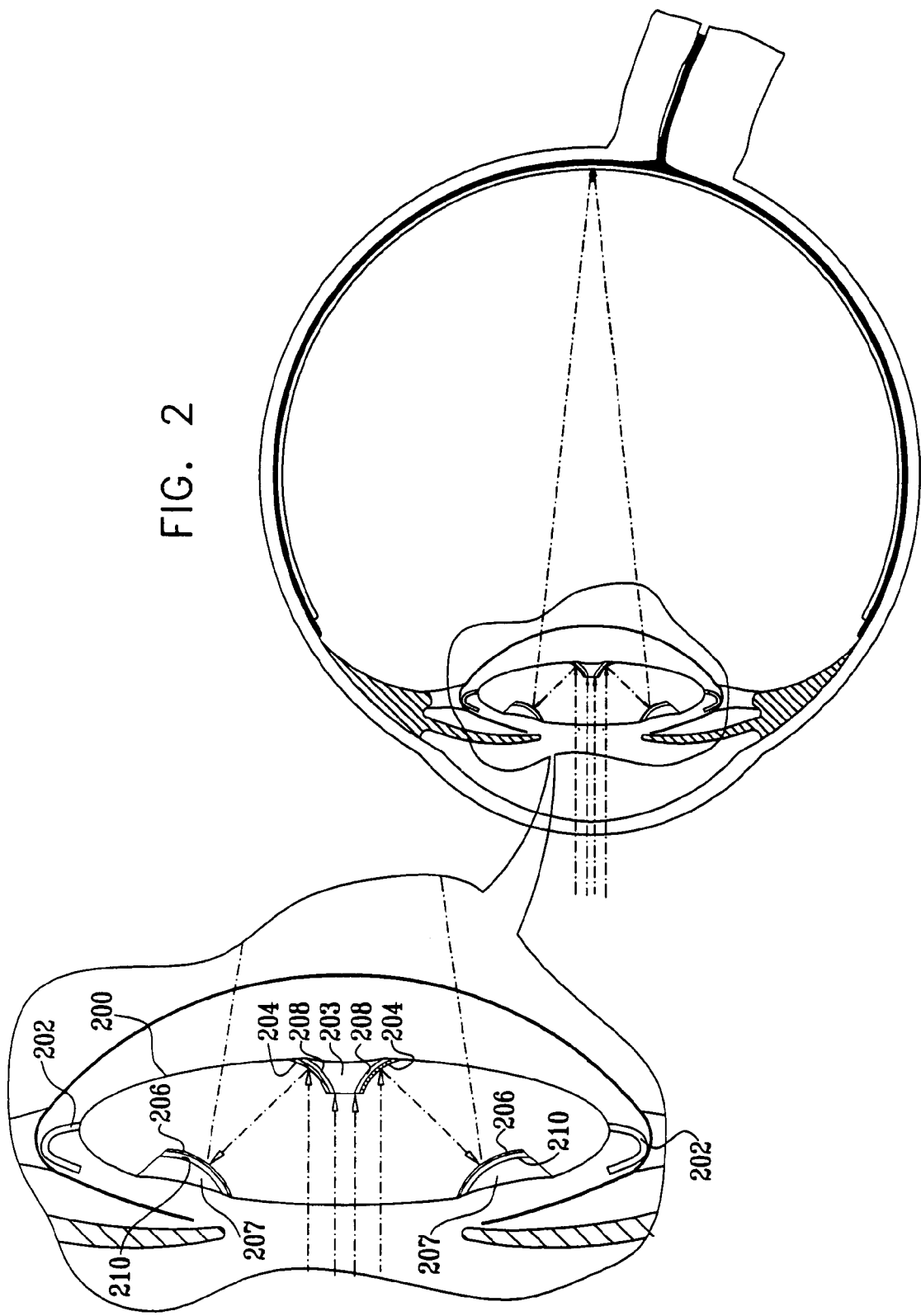
FIG. 2 is a simplified sectional illustration of an implanted intraocular implant constructed and operative in accordance with another preferred embodiment of the present invention.

Reference is now made to FIG. 2, which is a simplified sectional illustration of an implanted intraocular implant constructed and operative in accordance with another preferred embodiment of the present invention. As seen in FIG. 2, the implant preferably comprises a generally light transparent implant body 200, preferably formed of rigid plastic, such as PMMA, and having a generally oval cross section, as seen in FIG. 2, which is supported by haptics 202. Body 200 is generally solid and is formed with a plurality of indents. Located at a first indent 203 is an outwardly facing, generally truncated, circumferentially symmetric concave mirror 204. Mirror 204 is operative to reflect and focus light impinging thereon from the outside to an inwardly facing peripherally disposed, circumferentially symmetric convex mirror 206, formed at a second indent 207, which mirror 206, in turn, directs the light to the retina. It is appreciated that implant body 200 may have optical power and may help direct the light from a scene to the retina.

Mirrors 204 and 206 are preferably formed by coating suitably curved surfaces of body 200 at respective indents 203 and 207 with reflective materials, such as metallic materials which conventionally contain bio-incompatible materials. Indents 203 and 207 are hermetically sealed outwardly of respective mirrors 204 and 206, with suitable sealing layers 208 and 210 respectively, such as plastic, glass or other suitable bio-compatible transparent material, such as a sprayable transparent material. This hermetic sealing enables mirrors 204 and 206 to be employed in accordance with a preferred embodiment of the present invention and prevents contamination of the interior of the eye by the bio-incompatible materials.

It is appreciated that implant body 200 may include a solid transparent interior or a frame including a hollow interior and may be formed as a sealed transparent capsule or other suitable construction.

Figure 3:
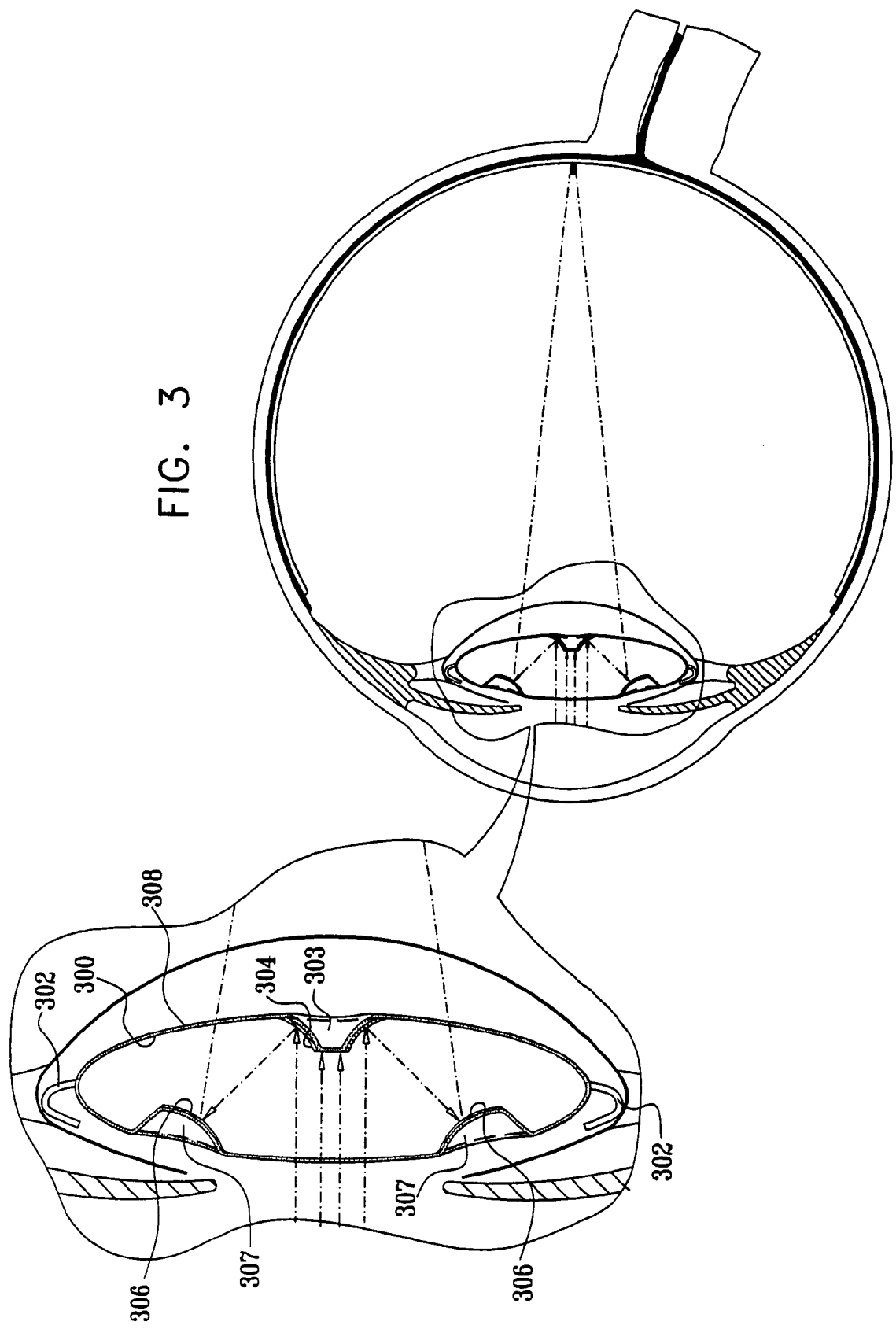
FIG. 3 is a simplified sectional illustration of an implanted intraocular implant constructed and operative in accordance with yet another preferred embodiment of the present invention.

Reference is now made to FIG. 3, which is a simplified sectional illustration of an implanted intraocular implant constructed and operative in accordance with yet another preferred embodiment of the present invention. As seen in FIG. 3, the implant preferably comprises a generally light transparent implant body 300, preferably formed of rigid plastic, such as PMMA, and having a generally oval cross section, as seen in FIG. 3, which is supported by haptics 302. Body 300 is generally solid and is formed with a plurality of indents. Located at a first indent 303 is an outwardly facing generally truncated, circumferentially symmetric concave mirror 304. Mirror 304 is operative to reflect and focus light impinging thereon from the outside to an inwardly facing peripherally disposed, circumferentially symmetric convex mirror 306, formed at a second indent 307, which mirror 306, in turn, directs the light to the retina.

Mirrors 304 and 306 are preferably formed by coating suitably curved surfaces of body 300 at respective indents 303 and 307 with reflective materials, such as metallic materials which conventionally contain bio-incompatible materials. The entire body 300 is hermetically sealed outwardly of respective mirrors 304 and 306, with a suitable sealing layer 308, such as plastic, glass or other suitable bio-compatible transparent material. This hermetic sealing enables mirrors 304 and 306 to be employed in accordance with a preferred embodiment of the present invention and prevents contamination of the interior of the eye by the bio-incompatible materials.

It is appreciated that implant body 300 may include a solid transparent interior or a frame including a hollow interior and may be formed as a sealed transparent capsule or other suitable construction.

It is also appreciated that either or both of implant body 300 and sealing layer 308 may have optical power and may help direct the light from a scene to the retina.

Reference is now made to FIG. 4, which is a simplified sectional illustration of an implanted intraocular implant constructed and operative in accordance with still another preferred embodiment of the present invention. As seen in FIG. 4, the implant preferably comprises a generally light transparent implant body 400, preferably formed of rigid plastic, such as PMMA, and having a generally oval cross section, as seen in FIG. 4, which is supported by haptics 402. Body 400 is generally solid and is formed with a plurality of indents. Located at a first indent 403 is an outwardly facing, generally truncated, circumferentially symmetric concave mirror 404. Mirror 404 is operative to reflect and focus light impinging thereon from the outside to an inwardly facing, peripherally disposed, circumferentially symmetric convex mirror 406, formed at a second indent 407, which mirror 406, in turn, directs the light to the retina. It is appreciated that implant body 400 may have optical power and may help direct the light from a scene to the retina.

Mirrors 404 and 406 are preferably formed separately from body 400 and placed at respective indents 403 and 407. Mirrors 404 and 406 are preferably formed with reflective materials, such as metallic materials, which conventionally contain bio-incompatible materials. Mirrors 404 and 406 are hermetically sealed, with suitable coatings 408 and 410 respectively, such as plastic, glass or other suitable bio-compatible transparent material. This hermetic sealing enables mirrors 404 and 406 to be employed in accordance with a preferred embodiment of the present invention and prevents contamination of the interior of the eye by the bio-incompatible materials.

It is appreciated that implant body 400 may include a solid transparent interior or a frame including a hollow interior and may be formed as a sealed transparent capsule or other suitable construction.

Figure 5A:
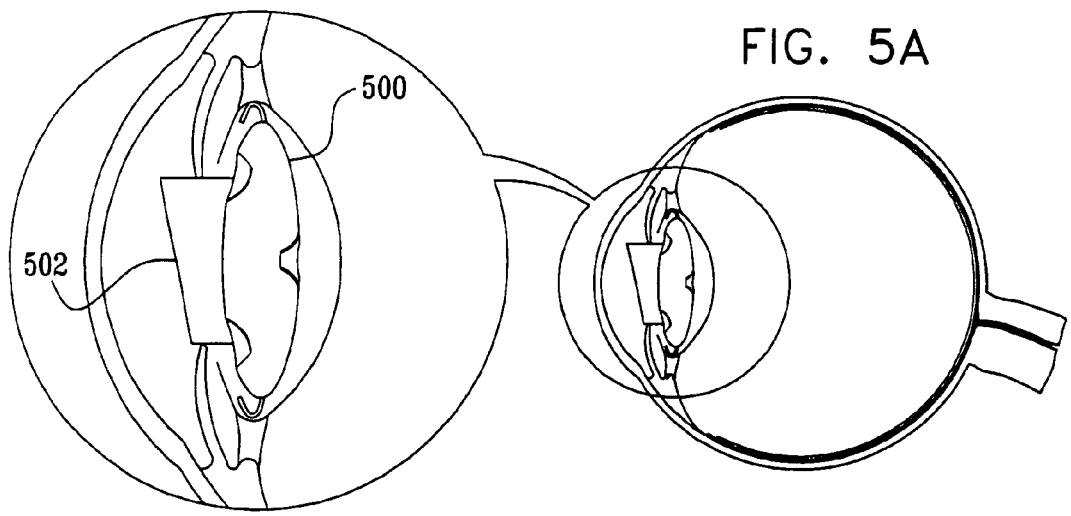
FIGS. 5A, 5B, 5C, 5D and 5E are simplified sectional illustrations of five alternative embodiments of an implanted intraocular implant including an iris restrictor.

Reference is now made to FIGS. 5A, 5B, 5C, 5D and 5E, which are simplified sectional illustrations of five alternative embodiments of an implanted intraocular implant including an iris restrictor. Turning to FIG. 5A, it is seen that an intraocular implant 500 of the type described hereinabove in any of FIGS. 1-4 is combined with an iris restrictor 502 in the form of an optical prism operative to deflect light entering implant 500, which also keeps the patient's pupil opened all of the time and is optically asymmetric. The iris restrictor 502 is located outside of the lens capsule and is attached to intraocular implant 500.

Figure 5B:
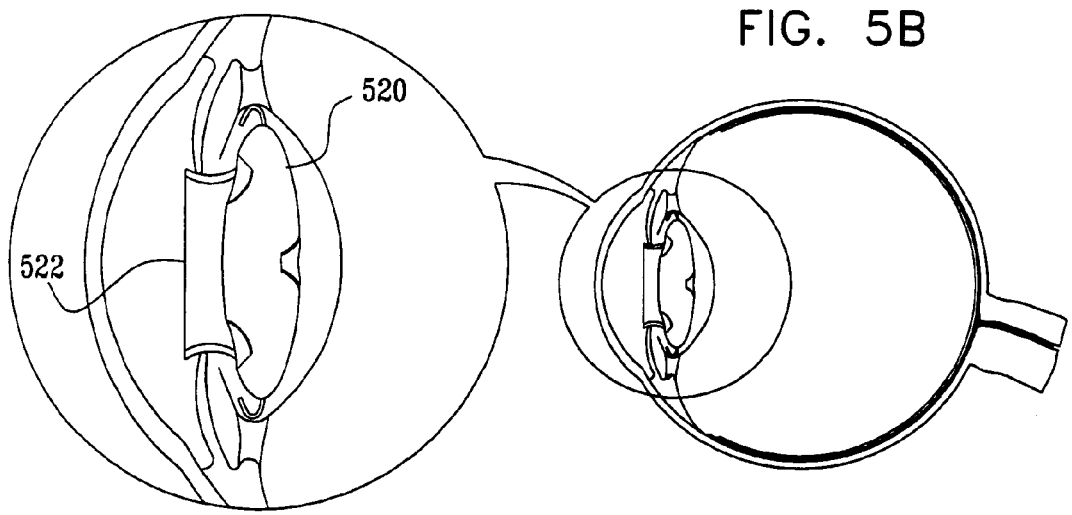

FIG. 5B shows an intraocular implant 520 of the type described hereinabove in any of FIGS. 1-4 combined with an iris restrictor 522 in the form of a hollow enclosure, such as a ring or other suitable shape, which keeps the patient's pupil opened all of the time and is optically symmetric. The iris restrictor 522 is located outside of the lens capsule and is attached to intraocular implant 520.

Figure 5C:
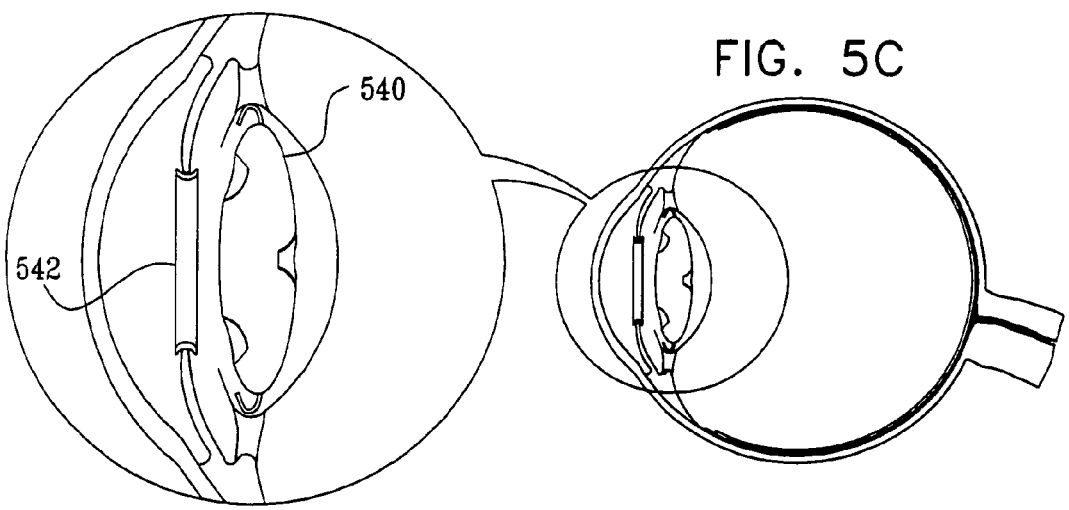

FIG. 5C shows an intraocular implant 540 of the type described hereinabove in any of FIGS. 1-4 combined with an iris restrictor 542 in the form of a hollow enclosure, such as a ring or other suitable shape, which keeps the patient's pupil opened all of the time and is optically symmetric. The iris restrictor 542 is located outside of the lens capsule and is sutured to or snapped onto the patient's iris.

Figure 5D:
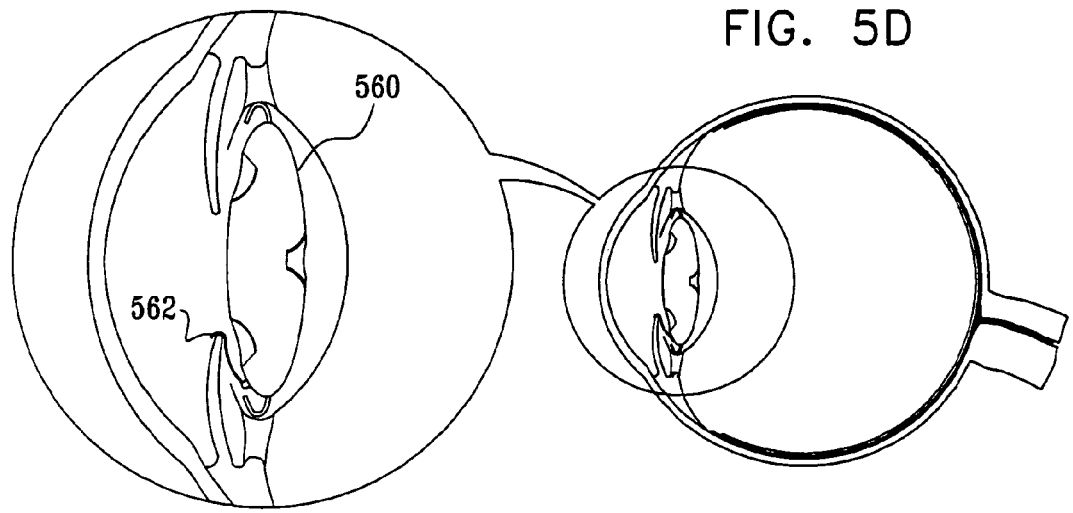

FIG. 5D shows an intraocular implant 560 of the type described hereinabove in any of FIGS. 1-4 combined with an iris restrictor 562 in the form of a hook, which keeps the patient's pupil opened and off center, all of the time. The iris restrictor 562 is located outside of the lens capsule and is attached to intraocular implant 560.

Figure 5E:
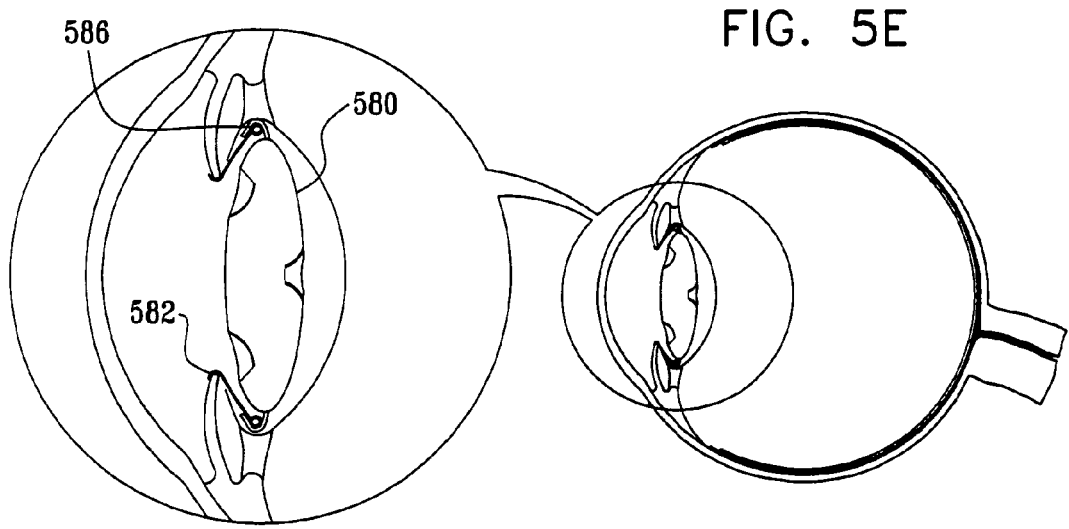

FIG. 5E shows an intraocular implant 580 of the type described hereinabove in any of FIGS. 1-4 combined with an iris restrictor 582 in the form of a peripheral retainer, which keeps the patient's pupil opened all of the time. The iris restrictor 582 is located outside of the lens capsule and is mounted onto a ring 586 implanted into the patient's eye.

Figure 6:
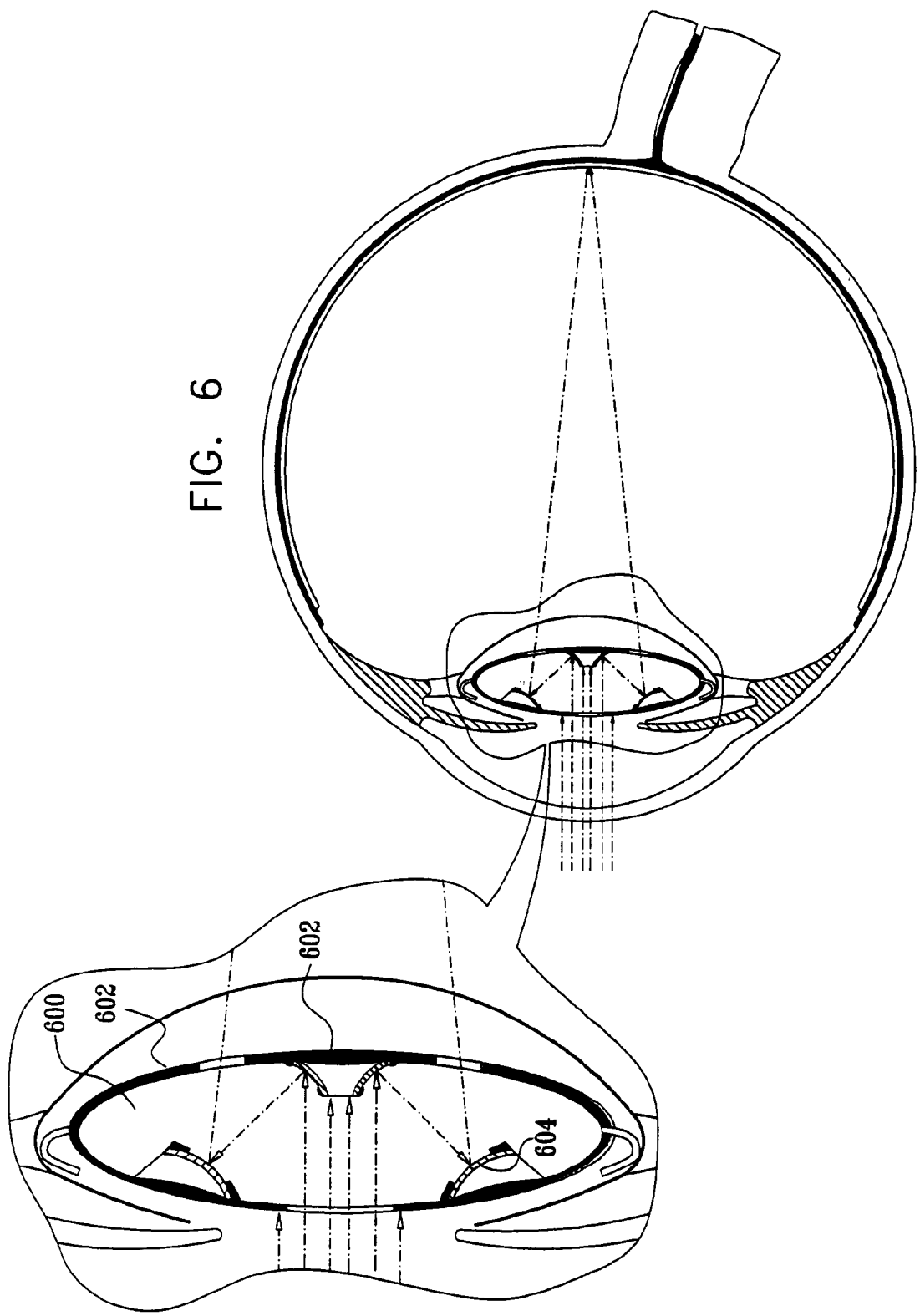
FIG. 6 is a simplified sectional illustration of an implanted intraocular implant including at least one light restrictor, in accordance with a preferred embodiment of the present invention.

Reference is now made to FIG. 6, which is a simplified sectional illustration of an implanted intraocular implant including at least one light restrictor, in accordance with a preferred embodiment of the present invention. The embodiment of FIG. 6 preferably includes an intraocular implant 600 of the type described hereinabove with reference to any of FIGS. 1-4 and may be combined with an iris restrictor as shown for example in any of FIGS. 5A-5E.

In the embodiment of FIG. 6, one or more light restrictors 602 are provided, typically by a light impermeable coating formed on the outside surface of portions of the implant 600 or mirrors 604, so as to function as artificial irises preferably on both the entrance pupil and the exit pupil of the implant 600, thereby restricting light passing through the implant, such that generally only light which impinges on the mirrors 604 of the implant reaches the retina, when the implant is implanted in a patient. Alternatively, light restrictors 602 may be formed by coating an inside surface of implant 600.

Figure 7:
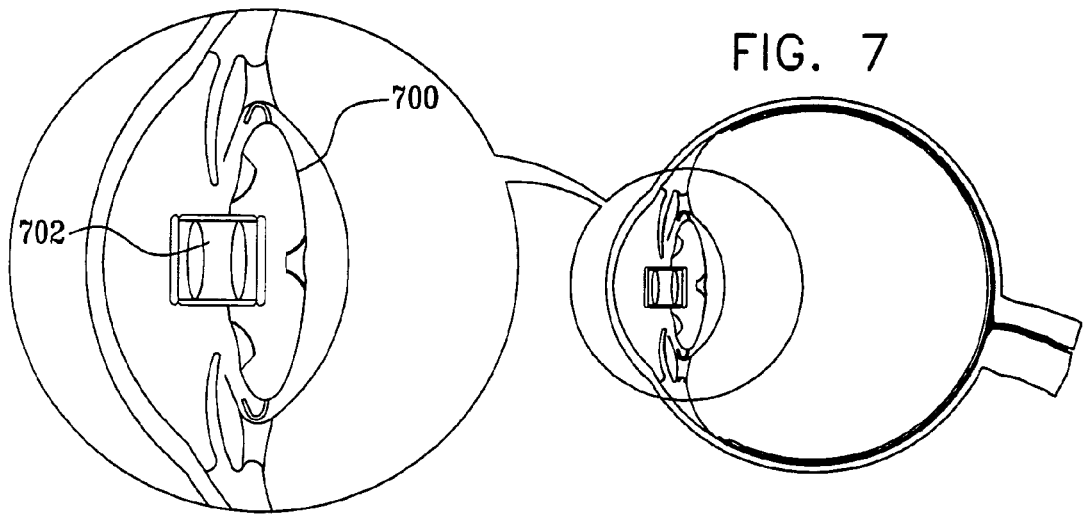
FIG. 7 is a simplified sectional illustration of an implanted intraocular implant including at least one encapsulated lens and a plurality of mirrors, in accordance with a preferred embodiment of the present invention.

Reference is now made to FIG. 7, which is a simplified sectional illustration of an implanted intraocular implant including at least one encapsulated lens and a plurality of mirrors, in accordance with a preferred embodiment of the present invention. The embodiment of FIG. 7 preferably includes an intraocular implant 700 of the type described hereinabove with reference to any of FIGS. 1-4 and may be combined with an iris restrictor as shown for example in any of FIGS. 5A-5E and with a light restrictor, as shown, for example in FIG. 6.

The implant of FIG. 7 also preferably includes external lenses, such as a telescope 702, preferably of the type described in any of applicant's published patent documents including U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793, the disclosures of which are hereby incorporated by reference, mounted onto implant 700 and extending outwardly of the lens capsule.

Figure 8:
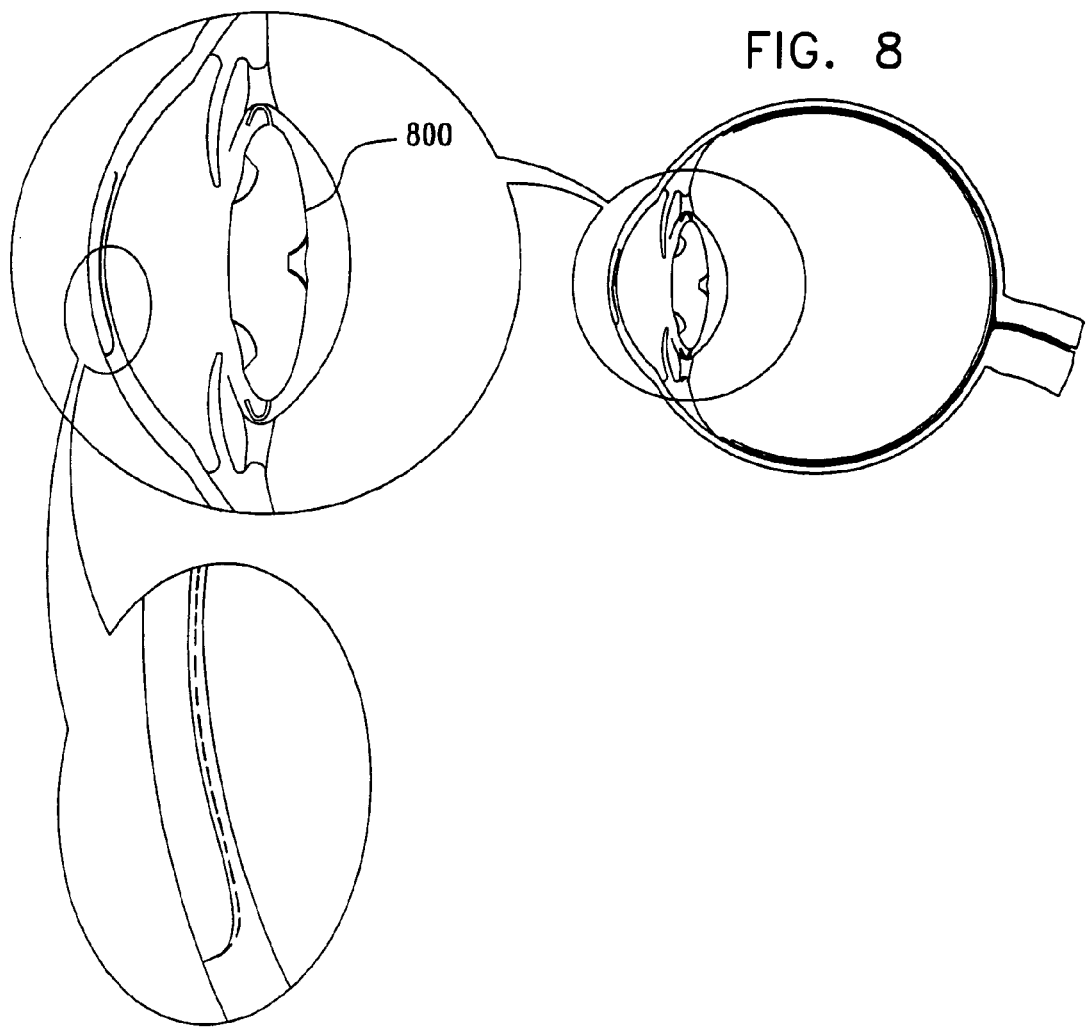
FIG. 8 is a simplified sectional illustration of an implanted intraocular implant of the type shown in any of the preceding figures implanted in an eye which has undergone refraction surgery, in accordance with a preferred embodiment of the present invention.

Reference is now made to FIG. 8, which is a simplified sectional illustration of an implanted intraocular implant of the type shown in any of the preceding figures implanted in an eye which has undergone refraction surgery, in accordance with a preferred embodiment of the present invention. The embodiment of FIG. 8 preferably includes an intraocular implant 800 of the type described hereinabove with reference to any of FIGS. 1-4 and may be combined with an iris restrictor as shown for example in any of FIGS. 5A-5E and with a light restrictor, as shown, for example in FIG. 6. The optical characteristics of the implant 800 are adapted to the condition and functionality of the patient's eye following such refractive surgery and are specifically configured to work with a reshaped cornea formed by the refractive surgery.

Figure 9:
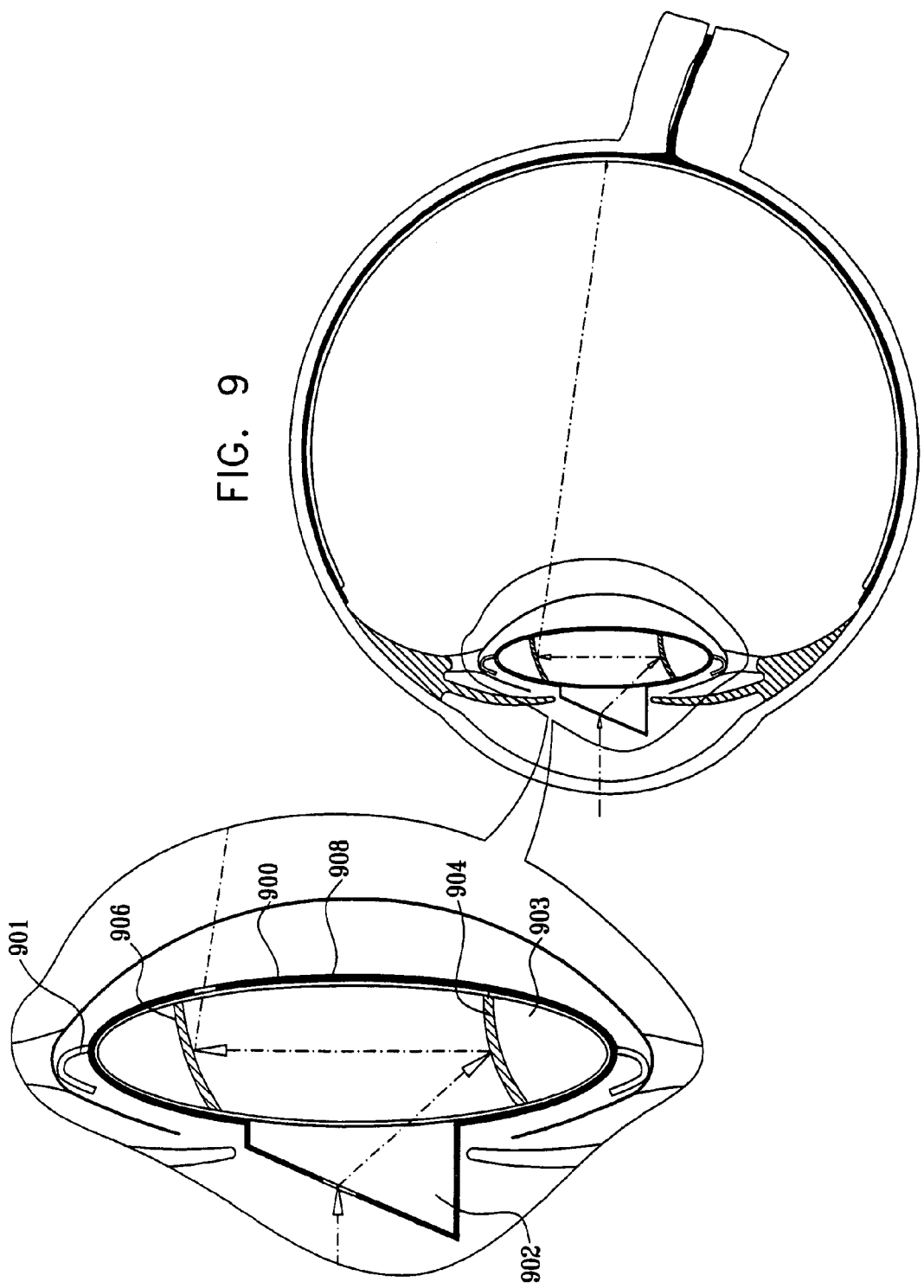
FIG. 9 is a simplified sectional illustration of an implanted intraocular implant including a prism and a plurality of mirrors, a bio-compatible housing and light restrictors arranged in a more preferred embodiment of the invention.

Reference is now made to FIG. 9, which is a simplified sectional illustration of an implanted intraocular implant including a prism and a plurality of mirrors, a bio-compatible housing and light restrictors arranged in a more preferred embodiment of the present invention.

As seen in FIG. 9, the implant preferably comprises a generally light transparent implant enclosure 900, preferably formed of rigid plastic, such as PMMA, and having a generally oval cross section, as seen in FIG. 9, which is supported by haptics 901. The interior of implant enclosure 900 is hermetically sealed from the outside thereof.

Mounted onto enclosure 900 and facing the outside is a prism 902 which directs light received from a scene inwardly and sidewise towards the interior of enclosure 900. Located within implant enclosure 900 and mounted therein is a transparent implant body 903 on which is formed an outwardly and sideways facing convex mirror 904. Mirror 904 is operative to reflect light impinging thereon from the outside via prism 902 onto an inwardly and sideways facing concave mirror 906, also formed on body 903, which mirror 906, in turn, directs the light to the retina. It is appreciated that either or both of enclosure 900 and implant body 903 may have optical power and may help direct the light from a scene to the retina.

As in embodiments described hereinabove, it a particular feature of the present invention that mirrors 904 and 906 are employed therein, inasmuch as mirrors 904 and 906 conventionally contain bio-incompatible materials. The hermetic sealing of implant body 903 enables their use in accordance with a preferred embodiment of the present invention and prevents contamination of the interior of the eye by the bio-incompatible materials.

As seen further in FIG. 9, implant body 903 also preferably includes one or more light restrictors 908, thereby restricting light passing through the implant, such that generally only light which impinges on the mirrors 904 and 906 of the implant reaches the retina, when the implant is implanted in a patient.

Alternatively, implant enclosure 900 may be obviated and prism 902 mounted directly onto implant body 903. In this embodiment, mirrors 904 and 906 may be formed by coating suitable portions of implant body 903 with reflective materials and hermetically sealing mirrors 904 and 906, similar to mirrors 204 and 206 of FIG. 2. Alternatively, mirrors 904 and 906 may be formed by coating suitable portions of implant body 903 with reflective materials and hermetically sealing implant body 903, similar to mirrors 304 and 306 of FIG. 3. As a further alternative, mirrors 904 and 906 may be formed separately from implant body 903 and hermetically sealed prior to placement in implant body 903, similar to mirrors 404 and 406 of FIG. 4.

It is appreciated that implant body 903 may include a solid transparent interior or a frame including a hollow interior and may be formed as a sealed transparent capsule or other construction suitable for maintaining mirrors 904 and 906 in proper alignment.

It will be appreciated by persons skilled in the art that the present invention is not limited to what has been particularly shown and described hereinabove. Rather the scope of the present invention includes both combinations and subcombinations of features described hereinabove as well as variations and modifications thereof which would occur to a person skilled in the art upon reading the foregoing description, taken together with the drawings, and which are not in the prior art.

The invention claimed is:

1. An intraocular implant comprising:
    a transparent body;
    a plurality of mirrors, including mirrors having non-zero optical power, being operative, when said implant is implanted, for receiving light from a scene and focusing said light onto a retina, said plurality of mirrors being formed on an outwardly facing surface of said transparent body;
    at least one enclosure, enclosing said plurality of mirrors and said transparent body; and
    at least one light restrictor formed on a surface of said enclosure, arranged so as to restrict light passing through said implant such that generally only light which impinges on said plurality of mirrors reaches the retina when said implant is implanted.

2. An intraocular implant according to claim 1 and wherein said plurality of mirrors is formed of a bio-incompatible material.

3. An intraocular implant according to claim 2 and wherein said plurality of mirrors is hermetically sealed to prevent contamination of the aqueous environment in the interior of the eye by said bio-incompatible material.

4. An intraocular implant according to claim 1, wherein said implant also includes a prism mounted onto said at least one enclosure and operative for receiving said light from said scene and directing said light on said plurality of mirrors.

5. An intraocular implant according to claim 1 and wherein at least one of said transparent body and said at least one enclosure has optical power.

6. An intraocular implant according to claim 1 and wherein said plurality of mirrors formed on said transparent body.

7. An intraocular implant according to claim 1 and wherein said transparent body comprises a frame including a hollow interior.

\* \* \* \* \*